United States Patent [19]
Wagner

[11] Patent Number: 4,584,379
[45] Date of Patent: Apr. 22, 1986

[54] ISOQUINOLINE THROMBOXANE SYNTHETASE INHIBITORS

[75] Inventor: Eugene R. Wagner, Carmel, Ind.

[73] Assignee: Merrell Dow Pharmaceuticals Inc., Cincinnati, Ohio

[21] Appl. No.: 693,423

[22] Filed: Jan. 22, 1985

[51] Int. Cl.$^4$ .................................. C07D 217/14
[52] U.S. Cl. ............................................ 546/147
[58] Field of Search ................................. 546/147

[56] References Cited

U.S. PATENT DOCUMENTS

| | | | |
|---|---|---|---|
| 3,707,470 | 12/1972 | Sawa et al. | 546/147 |
| 3,994,907 | 11/1976 | Maeda et al. | 546/290 |
| 4,241,068 | 12/1980 | Schromm et al. | 546/141 |
| 4,260,611 | 4/1981 | Bartmann et al. | 546/147 |
| 4,373,104 | 2/1983 | Takáes et al. | 546/148 |

FOREIGN PATENT DOCUMENTS 2065121  6/1981  United Kingdom .

OTHER PUBLICATIONS

Derwent Abstract: 10254x/06.
Partridge, et al., "J. Chem. Soc.", 1964, pp. 3673-3678.
Djudovic, et al., "Pharmazie.," vol. 31(12), 1976, pp. 845-848.
Mertes, et al., "J. Med. Chem.", vol. 13(2), 1970, pp. 276-279.

*Primary Examiner*—Glennon H. Hollrah
*Assistant Examiner*—James H. Turnipseed
*Attorney, Agent, or Firm*—John J. Kolano

[57] ABSTRACT

4-[(4-Isoquinolinylmethyl)amino]benzoic acid derivatives useful as selective thromboxane synthetase inhibitors are described herein. The compounds are obtained from the appropriate 4-isoquinolinecarboxylic acid derivative and an aminobenzoic acid derivative. This gives the corresponding Schiff base which is then reduced to give the desired compounds.

4 Claims, No Drawings

ISOQUINOLINE THROMBOXANE SYNTHETASE INHIBITORS

Selective inhibition of thromboxane synthetase enzyme has been described previously in the literature. Specific structure is significant in that closely related compounds may not exhibit the same selective activity. The present invention is thus directed to compounds with such selective activity and having the following general formula

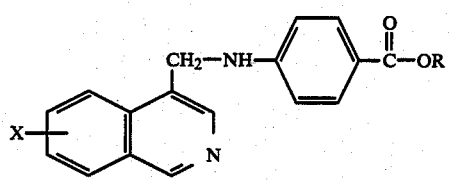

wherein R is hydrogen or lower alkyl and X is lower alkyl or lower alkoxy. The X substituent is attached on the benzene ring of the isoquinoline structure. The lower alkyl and lower alkoxy groups referred to above contain up to 4 carbon atoms and can be exemplified by methyl, ethyl, butyl, methoxy, ethoxy and butoxy.

Equivalent for the purposes of the present invention are salts of the above compounds with pharmaceutically acceptable acids. Examples of suitable acids are hydrochloric, hydrobromic, sulfuric, acetic and toluenesulfonic. It should be noted that those compounds wherein R is hydrogen are carboxylic acids and can thus exist in the form of internal salts although they may not be specifically named in that way. In addition, even though the internal salt form may exist, the compounds contain a second basic nitrogen group which could form a further salt with another acid as discussed above.

The compounds of the present invention are prepared by the reaction of an appropriate 4-isoquinolinecarboxaldehyde with a 4-aminobenzoic acid ester. The reaction is carried out with heating in an inert solvent such as toluene in the presence of a catalytic amount of acid. This reaction gives the Schiff base corresponding to the starting material together with water which is removed from the reaction mixture as it is formed. The Schiff base is then reduced to give the desired esters of the present application. Sodium borohydride is a preferred reducing agent for this purpose. To obtain the free carboxylic acids, the esters are saponified by standard procedure. Thus, for example, sodium hydroxide in aqueous ethanol can be used for the saponification.

The carboxaldehydes used as the starting material above can be obtained from the corresponding 4-bromoisoquinoline which is converted to the corresponding organometallic compound followed by reaction with dimethylformamide. n-Butyllithium (in hexane) is an example of a reagent useful in the preparation of the organometallic compound.

Thromboxane $A_2$ is a powerful vasoconstrictor and proaggregatory substance in that it causes platelet aggregation. Inhibition of this enzyme would thus be useful but only if it acted selectively without significantly inhibiting the prostacyclin synthetase and cyclo-oxygenase enzymes. Without specific selective inhibitory activity, other processes could take place and produce effects which would obscure the desired inhibition.

The novel compounds of this invention are thus active as selective inhibitors of the thromboxane synthetase enzyme system. Accordingly, the novel compounds are useful for administration to mammals, including humans, when it is desirable medically to inhibit this enzyme system.

The compounds are thus useful whenever it is desired to inhibit platelet aggregation, reduce the adhesive character of platelets, and remove or prevent the formation of thrombi in mammals, including man, rabbits, dogs and rats. As a result, these compounds would find use in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, the compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg/kg of body weight per day are used, the exact dose depending on the age, weight and condition of the patient or animal, and on the frequency and route of administration.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maize-starch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Pa.

The specific inhibitory activity of the present compounds can be determined by the following procedures. For platelet aggregation, blood was collected from normal volunteers into sodium citrate (3.8% w/v) 9:1. The indicated volunteers had not ingested aspirin or other non-steroidal anti-inflammatory drugs for at least 7 days. Platelet rich plasma was prepared from the blood by centrifugation at 200×g for 15 minutes. This plasma was centrifuged at 10,000×g for 2 minutes to obtain platelet poor plasma blank. The platelet rich plasma was incubated at 37° C. for 60 seconds prior to addition of vehicle or compound. The platelet rich plasma was then incubated for an additional 60 seconds prior to the addition of arachidonic acid or ADP. Aliquots (50 μl) were removed at 30 and 60 seconds after the addition of arachidonic acid for determination of iTXB$_2$. Platelet aggregation was monitored in a Model 300 Chronolog aggregometer using the method of Born. The isoquinoline of the present invention (reference to the isoquinoline here and below means 4-[(4-isoquinolinylmethyl)amino]benzoic acid) significantly inhibited the rate of arachidonic acid induced platelet aggregation at concentration of 1 mM and 0.5 mM. At 1 mM, it had a marked effect on ADP induced platelet aggregation as compared to control and it significantly reduced the amounts of iTXB$_2$ produced at 30 and 60 seconds during arachidonic acid induced platelet aggregation. The isoquinoline (1000 μM) also reduced ADP aggregation by 30% at 60 seconds.

The following procedure can be used to demonstrate the selectivity of the above inhibition in a test involving $^{14}$C-arachidonic acid metabolism. Washed platelets (400 μl) prepared as above were placed in a cuvette. Either vehicle (50 μl), isoquinoline test compound, or indomethacin was then added. After incubation for 55 seconds at 37° C., 50 μl of calcium chloride (5 mM) was added and, at 60 seconds, 50 μl of $^{14}$C-arachidonic acid (0.1 μCi, 0.4 mM) was added. Four minutes later, 80 μl of 10% formic acid was added to stop the reaction. The contents were then poured into 6.5 ml of ice-cold ethyl acetate and the cuvette was further rinsed twice with 1 ml of ethyl acetate. The samples were subsequently extracted as previously described. The dried extract was reconstituted in chloroform:methanol (2:1) and spotted onto TLC plates. PGE$_2$ PGF$_{2\alpha}$, TXB$_2$ (20 μg of each) were spotted as the reference. The plates were developed in a chloroform:methanol, acetic acid, water (90:8:1:0.8) solution. The R$_f$ values were consistent with those previously reported for the standards. Plates were scanned with a Packard Model 7201 Radio Chromatogram scanner. Each plate was visualized with iodine vapor, the R$_f$s noted and then 1 cm zones scraped and counted in a Beckman Liquid Scintillation spectrometer. The isoquinoline reduced the percentage of arachidonic acid converted to TXB$_2$ but did not affect the percent converted to PGE$_2$. The total amount of arachidonic acid metabolized via the cyclo-oxygenase pathway was not different from the vehicle controls. In contrast, indomethacin (50 μM) reduced the metabolism of [$^3$H]-arachidonic acid 78% compared to controls.

The following procedures were used to demonstrate in vivo activity. Varying doses of the test compound were administered intravenously to female Sprague-Dawley rats weighing between 250-300 g 30 minutes prior to obtaining blood. Pretreatment with the isoquinoline compound produced a dose dependent reduction in iTXB$_2$ production by whole blood. A dose of 10 mg/kg produced approximately a 50% inhibition of iTXB$_2$ production.

To establish if the test compound was a selective thromboxane synthetase inhibitor or a fatty acid cyclooxygenase inhibitor, the effects of the isoquinoline on endogenous arachidonic acid metabolism by microphages was assessed. The isoquinoline significantly reduced the basal synthesis of iTXB$_2$ by microphages at concentrations of 10 μM to 1000 μM. At most concentrations of isoquinoline, iPGE levels were significantly increased. The effect on i-6-keto-PGF$_\alpha$ levels was variable. At a concentration of 500 μm it inhibited i-6-keto-PGF$_\alpha$ formation and at 250 μm it increased its formation. At all other concentrations it had no affect. Thus, the isoquinoline appears to selectively inhibit thromboxane synthesis.

The following examples are presented to illustrate the present invention. They should not be construed as limiting it in any way.

EXAMPLE 1 n-Butyllithium in n-hexane (90 ml, 2.4 M) was added at room temperature to a mixture of 500 ml of anhydrous ether and 500 ml of tetrahydrofuran under nitrogen. The solution was cooled to −68° C. and there was added 20.8 g of 4-bromoisoquinoline portionwise over a period of 30 minutes while maintaining the temperature at about −67° C. When addition was complete, the dark brown solution was stirred at −68° C. for 30 minutes. Then, a solution of 73 g of dimethylformamide in 150 ml of tetrahydrofuran at −68° C. was added all at once. The temperature rose to −57° C. and the reaction turned lighter brown. The mixture was stirred in dry ice for 15 minutes and then 100 ml of chilled ethanol was added over a period of 5 minutes. This was followed by the addition of 100 ml of saturated ammonium chloride solution and then 100 ml of saturated aqueous sodium chloride solution. The solution was then warmed to room temperature, the layers separated and the aqueous layer was washed once with ether. The organic layers were combined and dried over sodium sulfate and the solvent was evaporated. The resulting orange-brown oil was then dried. The residue was recrystallized from ethanol to give 4-isoquinolinecarboxaldehyde melting at about 104°-105° C.

EXAMPLE 2

A mixture of 8.0 g of 4-isoquinolinecarboxaldehyde and 8.4 g of ethyl 4-aminobenzoate in 100 ml of toluene was refluxed in the presence of a catalytic amount of 4-toluenesulfonic acid. The water which formed was collected until no more was formed. The toluene was then removed under reduced pressure and the resulting residue was dissolved in 100 ml of ethanol. To the solution was then added 2 g of sodium borohydride and the mixture was refluxed for 30 minutes and then stirred at room temperature for 16 hours. The solution was concentrated to a volume of 50 ml and then poured into 1 liter of water. A thick pasty precipitate formed. The water was decanted and the precipitate was dissolved in methylene chloride and dried over sodium sulfate and the solvent was evaporated. The dark residue was triturated with 1:1 methylene chloride/hexane whereupon crystals formed. The solid was then separated by filtration and washed with additional solvent before further drying. Recrystallization of the solid from 50 ml of ethanol then gave ethyl 4-[(4-isoquinolinylmethyl)amino]benzoate melting at about 140°-141.5° C.

EXAMPLE 3

A mixture of 3.5 g of ethyl 4-[(isoquinolinylmethyl)amino]benzoate in 100 ml of 1N aqueous sodium hydroxide and 50 ml of ethanol was refluxed until a clear solution formed. The solution was poured into 1 liter of water and acidified to pH 6. A crystalline solid formed. This was separated and dried and then recrystallized from a mixture of 200 ml of acetonitrile and 50 ml of water to give 4-[(4-isoquinolinylmethyl)amino]benzoic acid melting at about 237°–240° C.

What is claimed is:

1. A compound of the formula:

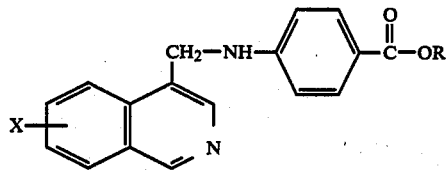

wherein R is hydrogen or lower alkyl and X is lower alkyl or lower alkoxy.

2. A compound according to claim 1 which has the formula:

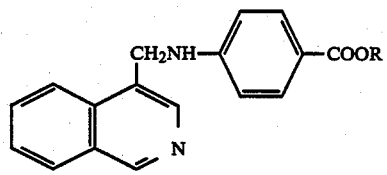

wherein R is hydrogen or lower alkyl of 1 to 4 carbon atoms.

3. A compound according to claim 1 which is 4-[(4-isoquinolylmethyl)amino]benzoic acid.

4. A compound according to claim 1 which is ethyl 4-[(4-isoquinolylmethyl)amino]benzoate.

* * * * *